US00PP08565P

United States Patent [19]

Bak et al.

[11] Patent Number: Plant 8,565

[45] Date of Patent: Jan. 25, 1994

[54] GUZMANIA PLANT NAMED SAMBA

[75] Inventors: Gerardus J. Bak, Assendelft; Nicolaas D. Steur, Oude Niedorp; Elly Bak, Rijsenhout, all of Netherlands

[73] Assignee: Corn. Bak B.V., Assendelft, Netherlands

[21] Appl. No.: 876

[22] Filed: Jan. 5, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new cultivar of Guzmania named Samba, characterized by its primary bracts which are intense yellow-orange in color, with darker orange tips; somewhat darker yellow-orange flowers; superior bract production, and its blooming time of 13 weeks following natural induction or acetylene treatment.

2 Drawing Sheets

The present invention relates to a new and distinct cultivar of Guzmania, hereinafter referred to by the cultivar name Samba. Guzmania comprise a genus within the family bromeliaceae. The new cultivar is a hybrid resulting from a cross of unnamed parents identified below.

Guzmania comprise a genus of over 100 species of evergreen perennials suitable for cultivation in the home or under glass. Guzmania are prerdominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania varies considerably but is generally in the orange, red and red-purple ranges. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

Samba is a hybrid and is a product of a planned breeding program conducted in Assendelft, the Netherlands. Samba was originated by the inventors from a hybridization made in such program. The female or seed parent was a selection of *Guzmania lingulata* minor identified by the Code No. 62101. The male or pollen parent of Samba was a selection of *Guzmania wittmackii* identified by Code No. 62136. Both parents are proprietary, unreleased lines.

Samba was discovered and selected within the progeny of the stated parentage by the inventors in 1982 in a controlled environment in Assendelft, and the plant flowered for the first time in 1985.

The first act of asexual reproduction of Samba was performed by the inventors in 1985, with the reproduction being effected through off-shoots, at our facility in Assendelft, the Netherlands. Asexual reproduction by tissue culture began in 1986 and is the preferred reproduction technique. Horticultural examination of selected units initiated following propagation clearly demonstrated that the combination of characteristics as herein disclosed for Samba are firmly fixed and retained through successive generations of asexual reproduction.

Samba has not been observed under all possible environmental conditions. The phenotype may vary when grown under different environmental conditions with respect to temperature, light, humidity, fertilizer, and other factors without, however, any variation in the genotype.

The following observations, measurements and comparisons describe plants grown in Assendelft, the Netherlands under greenhouse conditions which approximate those generally used in commercial practice in the Netherlands.

The following traits have been repeatedly observed and are determined to be basic characteristics of Samba which in combination distinguish this Guzmania as a new and distinct cultivar:

1. Superior bract production.
2. The primary bracts are an attractive, intense yellow-orange in color, with orange tips.
3. Strong, relatively compact growth habit.
4. The flowers are slightly deeper yellow-orange in color, with each flower blooming 1 day and the total blooming period being six weeks.
5. Flowering can be controlled year around, starting approximately 13 weeks after natural induction or treatment with acetylene.

Samba is similar in certain respects to the commercial cultivar Grand Prix. The most significant differences are the yellow-orange inflorescence of Samba (compared to red in Grand Prix), and the size of the inflorescence on the stalk. In Samba, the flowered part of the inflorescence is shorter.

In the accompanying color photographic drawings, the photograph on sheet 1 comprises a side elevational view of the inflorescence and foliage characteristics of Samba. On sheet 2, the photograph at the top comprises an enlarged view of the inflorescence of Samba, and the bottom photograph comprises a still further enlarged showing of the flowers. The colors depicted in the photographs are as nearly true as possible with illustrations of this type.

In the following description, color references are made to The Royal Horticultural Society Colour Chart, except where terms of ordinary dictionary significance are used.

Classification:

*Botanical.*—Guzmania hybrid cv Samba.

PLANT

Form: Funnel form rosette.

Height: Approximately 45 cm high at time of flowering.

Growth habit: Stemless.

Foliage:

*Size of leaf.*—Length, approximately 35 cm; width, approximately 3 cm.

*Shape of leaf.*—Linear-lanceolate.

*Surface texture.*—Smooth.

*Color.*—Upperside 137A; Underside 137B; color can change somewhat depending on environmental conditions.

BRACTS

Bract shape: Lanceolate.

Bract size: Scape bracts are approximately 10–25 cm in length and 3 cm wide; primary bracts are 4–10 cm in length and 3 cm wide, and floral bracts are approximately 5–6 cm in length.

*Number of bracts.*—Approximately 12 primary bracts and 8 scape bracts.

*Margin.*—Entire.

*Color.*—Primary bracts 17A, with bract ends 33A–169A; color will slightly fade with maturity.

FLOWERS

Borne (stalks): Erect.

Shape of inflorescence: Compound.

Size of inflorescence on stalk: Approximately 15 cm.

Individual flowers or petals: (Mostly disposed within the floral bracts hidden behind the primary bracts.)

*Length.*—Approximately 5.5 cm.

*Width.*—Approximately 0.5 cm.

*Quantity.*—Approximately 80 flowers divide over approximately 12 branches depending on the size of the plant.

*Color.*—17A–23A.

Time of blooming: A fully grown plant can bloom at any time during the year starting approximately 13 weeks after natural induction or through treatment with acetylene.

Duration of blooms: Each flower blooms 1 day and the total blooming period is approximately 6 weeks.

REPRODUCTIVE ORGANS

Ovaries: Superior.

Stamens: Six (6) in number, typical.

SEED CHARACTERISTICS

Samba is a sterile hybrid, therefore no fruit or seed is produced.

I claim:

1. A new and distinct cultivar of Guzmania plant named Samba, as illustrated and described.

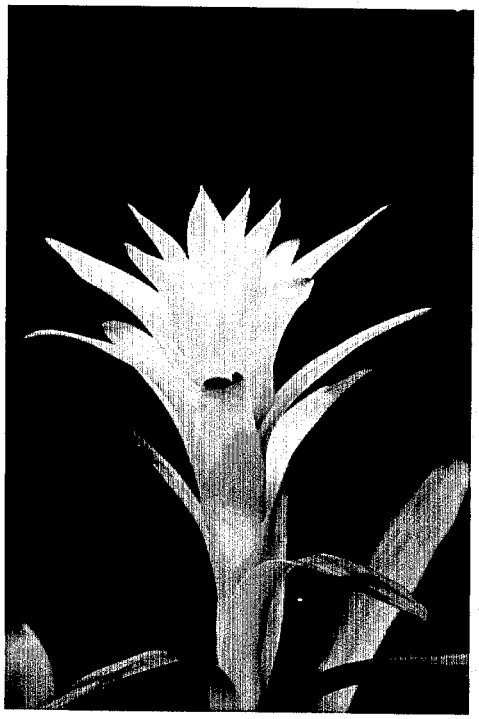
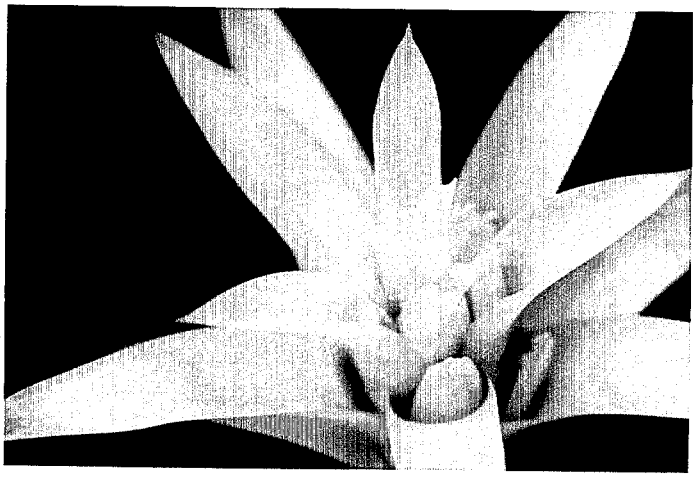

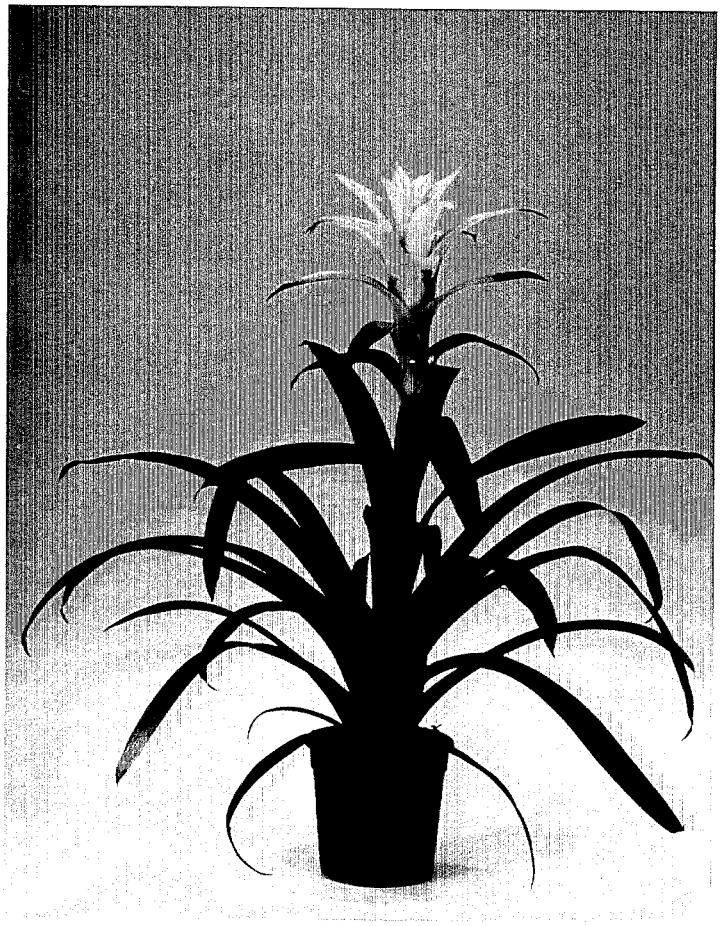

* * * * *